United States Patent [19]

Reid et al.

[11] Patent Number: 5,411,965
[45] Date of Patent: May 2, 1995

[54] USE OF DELTA OPIOID RECEPTOR ANTAGONISTS TO TREAT COCAINE ABUSE

[75] Inventors: Larry D. Reid, Troy, N.Y.; Philip S. Portoghese, St. Paul, Minn.; Frank Porreca, Tucson, Ariz.

[73] Assignee: Arizona Board of Regents, Tucson, Ariz.

[21] Appl. No.: 110,396

[22] Filed: Aug. 23, 1993

[51] Int. Cl.$^6$ ............................................. A61K 31/44
[52] U.S. Cl. ..................................................... 514/279
[58] Field of Search ........................................ 514/279

[56] References Cited

U.S. PATENT DOCUMENTS 4,816,586  3/1989  Portoghese et al. ................ 544/340

OTHER PUBLICATIONS

Bain et al., *Life Sciences*, 40, 1119 (1983).
Beach, *Can J. Psychol.*, 11, 104 (1957).
Belluzi et al., *Nature*, 266, 556 (1977).
Bilsky et al., *Life Sciences*, 50, PL–85 (1992).
Bilsky et al., *Pharmacol. Biochem. Behav.*, 37, 425 (1990).
Carr et al., *The Neuropharmacological Basis of Reward*, S. Leibman et al., eds., Oxford U. Press, N.Y., (1989).
Carroll et al., *J. Med. Chem.*, 35, 969 (1992).
Clark et al., *J. Med. Chem.*, 16, 1620 (1973).
Clouet et al., eds., "Mechanisms of Cocaine Abuse and Toxicity", NIDA Research Monograph (1988).
Cotton et al., *Eur. J. Pharmacol.*, 97, 331 (1984).
Drower et al., *J. Pharmacol. Exp. Ther.*, 259, 725 (1991).
Froehlich et al., *Alcoholism Clin. and Exp. Res.* Abstract 20, p. 315 (1991).
Garcia et al., *Brit J. Radiology*, 30, 318 (1957).
Gawin et al., *Arch. Gen Psychiatry*, 43, 107 (1986).
Glennon, *Psychopharmocology: The Third Generation of Progress*, H. Y. Meltzer, ed., Raven Press, N.Y. (1987).
Griffiths et al., in *Advances in Substance Abuse*, vol. 1, N. K. Mello, ed., UAI Press Inc., Greenwich, Conn. (1980).
Johanson et al., *Pharmacol. Rev.*, 41, 3 (1989).
Kozikowski et al., *Med. Chem. Res.*, 1, 312 (1991).
Martin, *Pharmacol. Rev.*, 35, 283 (1983).
Menkens et al., *Eur. J. Pharmacol.*, 219, 345 (1992).
Mucha et al., *Brain Res.*, 243, 91 (1982).
Musto, *Sci. Amer.*, 256, 40 (1991).
Portoghese et al., *J. Med. Chem.*, 31, 281 (1988).
Portoghese et al., *J. Med. Chem.*, 33, 1547 (1990).
Portoghese et al., *Eur. J. Pharmacol.*, 146, 185 (1988).
Portoghese et al., *J. Pharmacol. Exp. Ther.*, 258, 299 (1991).
Reid et al., *Life Sciences*, 52, 67 (1993).
Reid, *Methods of Assessing the Reinforcing Properties of Abused Drugs*, M. A. Bozarth, ed., Springer-Verlag, N.Y. (1987).
Reid et al., *Physiol. Psychol.* 4, 269 (1976).
Shaw et al., *Life Sci.*, 31, 1259 (1982).
Sofuoglu et al., *J. Pharmacol. Exp. Ther.*, 257, 676 (1991).
Spanagel et al., *J. Neurochem.*, 55, 1734 (1990).
Stapleton et al., *Physiol. Psychol.*, 7, 427 (1979).
Ukai et al., *Eur. J. Pharm.*, 231, 143 (1993).

*Primary Examiner*—Johann Richter
*Assistant Examiner*—John D. Peabody
*Attorney, Agent, or Firm*—Schwegman, Lundberg & Woessner

[57] ABSTRACT

A therapeutic method is provided to inhibit the use of cocaine by the administration of an effective amount of certain selective delta opioid receptor antagonists to a human patient in need of such treatment.

17 Claims, 5 Drawing Sheets

USE OF DELTA OPIOID RECEPTOR ANTAGONISTS TO TREAT COCAINE ABUSE

BACKGROUND OF THE INVENTION

This invention was made with the assistance of the Government under a grant from the National Institute on Drug Abuse (Grant No. DA04440). The U.S. Government has certain rights in the invention.

(R)-Cocaine or (−)-cocaine (1) is a plant alkaloid extractable from the leaves of *Erythroxylon coca*, or which can be chemically synthesized. It is one of the eight possible stereoisomeric forms of methyl 3-(benzoyloxy)-8-methyl-8-azabicyclo[3.2.1]octane-2-carboxylate.

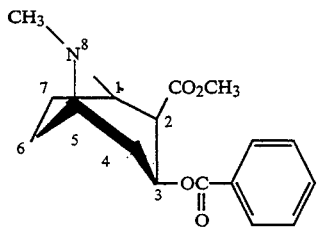

1

In both animals and humans, cocaine is one of the most addictive drugs known. The addictive properties of cocaine have recently led to a serious problem of cocaine abuse in the United States. See, D. F. Musto, *Opium, Cocaine and Marijuana in American History*, *Sci. Amer.*, 256, 40 (1991); D. Clouet et al., eds., "Mechanisms of Cocaine Abuse and Toxicity," *NIDA Research Monograph* (1988) at page 88; C. E. Johanson et al., *Pharmacol. Rev.*, 41, 3 (1989).

Cocaine has many physiological effects. It is a local anesthetic, and this property is responsible for its early legitimate use in medicine. However, many newer compounds have been developed that are superior to cocaine for this purpose. Cocaine is also a powerful vasoconstrictant and as such has some current use in medicine during nasal or throat surgery where control of bleeding is desired. Cocaine also has very potent effects on the sympathetic nervous system, and it is well known to increase heart rate and blood pressure. From the point of view of drug abuse, the most relevant effects of the drug documented in human subjects include its ability to produce euphoria and its ability to reinforce its own use. See, R. R. Griffiths et al., in *Advances in Substance Abuse*, Vol. 1, N. K. Mello, ed., UAI Press Inc., Greenwich, Conn. (1980) at pages 1–90. In addition to being a powerful reinforcer, cocaine also has properties common to other drugs subject to abuse. There is a psychological withdrawal syndrome that follows extended use of cocaine that is manifested by periods of depression and by periods of intense craving, which may prompt relapse into using cocaine extensively again. Drugs that might attenuate the depression of withdrawing from cocaine might therefore be of some utility in treating cocaine addiction. See, F. H. Gawin et al., *Arch. Gen. Psychiatry*, 43, 107 (1986).

The prototypical opioid antagonists, naloxone and naltrexone, are used primarily as pharmacologic research tools and for the reversal of toxic effects of opioids in case of overdose. However, naloxone has been reported to antagonize the threshold-lowering effect of cocaine for brain stimulation reward in the rat model by G. T. Bain et al., *Life Sciences*, 40, 1119 (1983). More recently, naltrexone has been reported to attenuate cocaine's reinforcing properties in a conditioned place preference study using rats by E. J. Bilsky et al., *Life Sciences*, 50, PL-85 (1992). Since these antagonists act at multiple opioid receptors, their application in human therapy may be limited, due to undesirable side effects, such as producing depression.

The widely accepted theory that three different types [mu (μ), delta (δ), kappa (κ)] of opioid receptors mediate the effects of opioids raises the possibility that highly selective exogenous opioid agonists or antagonists might be developed. See W. R. Martin, *Pharmacol. Rev.*, 35, 283 (1983). In fact, in recent years, some progress has been made in the development of selective opioid antagonists. Pentapeptides structurally related to the enkephalins have been reported to be highly delta-selective opioid antagonists. Such compounds (e.g., ICI 174864) currently are employed as pharmacologic probes of receptor function and structure, but they possess the disadvantage of low potency and poor penetration into the central nervous system (CNS). See J. W. Shaw et al., *Life Sci.*, 31, 1259 (1982) and R. Cotton et al., *Eur. J. Pharmacol.*, 97, 331 (1984). Portoghese et al. (U.S. Pat. No. 4,816,586) disclose certain opiate analogs which possess high selectivity and potency at delta receptors. Certain of these compounds have been reported both to deter ethanol ingestion in an alcohol-preferring rat line and to block morphine tolerance and dependence in the rat model. See, J. C. Froehlich et al., *Alcoholism Clin. and Exp. Res.*, Abstract 20, page 315 (1991) and M. Sofuoglu et al., *J. Pharmacol. Exp. Ther.*, 257, 676 (1991).

Currently, there are no accepted drugs useful for the treatment of cocaine abuse. Thus, a continuing need exists for pharmacological approaches to the treatment of cocaine abuse. More specifically, a need exists for an effective method to prevent cocaine's positive reinforcement and/or dependence.

SUMMARY OF THE INVENTION

The present invention provides a method for treating cocaine use by a human comprising administering to said human in need of such treatment an amount of a compound of the formula I:

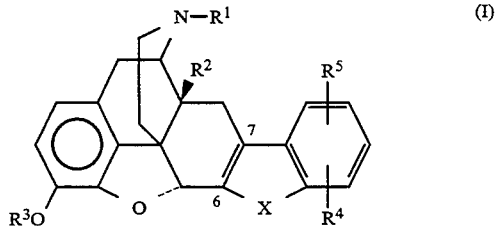

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(C_1-C_5)$alkyl; $R^3$ is H, $(C_1-C_5)$alkyl or $(C_1-C_5)$alkylCO; X is O, S or NY, wherein Y is H or $(C_1-C_5)$alkyl; and $R^4$ and $R^5$ are individually H, F, Cl, Br, NCS, $NO_2$, $NH_2$, $(C_1-C_5)$alkyl, or $(C_1-C_5)$alkoxy or together are benzo; and the pharmaceutically acceptable salts thereof, which amount is effective to inhibit said use. Preferably, the amount of said compound of formula I is effective to treat cocaine abuse or addiction, and may act by blocking or reducing the positive reinforcement and dependence caused by the use of cocaine by said human.

A preferred compound of formula I, disclosed in U.S. Pat. No. 4,816,586, has been named "naltrindole" or "NTI" (17-(cyclopropylmethyl)-6,7-dehydro-3,14β-dihydroxy-4,5α-epoxy-6,7-2′,3′-indolmorphinan) and has the formula:

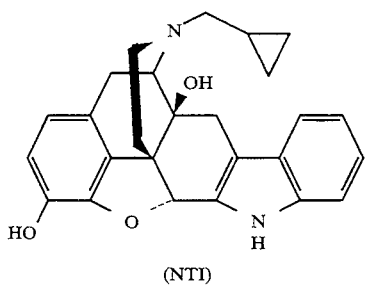

(NTI)

Another preferred compound of formula I is (17-(cyclopropylmethyl)-6,7-dehydro-3,14β-dihydroxy-4,5α-epoxy-6,7-2′,3′-benzo[b]furanomorphinan. See P. S. Portoghese et al., *J. Med. Chem.*, 31, 281 (1988). Another preferred compound of formula I is naltrindole 5′-isothiocyanate or "5′-NTII" (see, P. S. Portoghese et al., *J. Med. Chem.*, 33, 1547 (1990); *Eur. J. Pharmacol.*, 146, 185 (1988); *J. Med. Chem.*, 31, 281 (1988); *J. Pharmacol. Exp. Ther.*, 258, 299 (1991)). These compounds are selective δ-opioid receptor antagonists.

In another embodiment of the present method, cocaine use by a human patient, i.e., a human subject to or at risk of experiencing cocaine positive reinforcement or dependence, is treated with an effective amount of a compound of the formula (II):

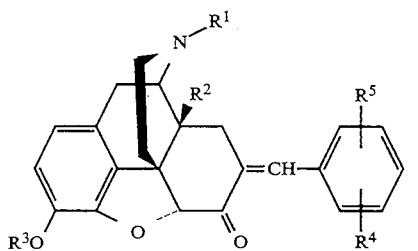

(II)

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(-C_1-C_5)$alkyl; $R^3$ is H, $(C_1-C_5)$alkyl or $(C_1-C_5)$alkylCO; and $R^4$ and $R^5$ are individually H, F, Cl, Br, $NO_2$, $NH_2$, NCS, $(C_1-C_5)$alkyl, $(C_1-C_5)$alkoxy or together are dioxymethylene ($-OCH_2O-$) or benzo; and the pharmaceutically acceptable salts thereof. A preferred compound of formula II is 7-benzylidenenaltrexone or "BNTX," wherein $R^1$ is cyclopropylmethyl, $R^2$ is OH, and $R^3=R^4=R^5=H$.

The present invention also provides a method of treating cocaine use by administering to a human in need of such treatment, an effective amount of a biologically active compound of formula III:

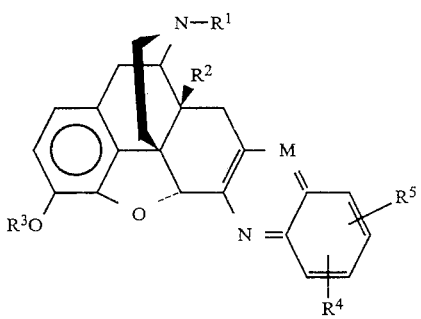

(III)

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(-C_1-C_5)$alkyl; $R^3$ is H, $(C_1-C_5)$alkyl or $((C_1-C_5)$alkyl)-C=O; M is N or CH, and $R^4$ and $R^5$ are as described for formula I hereinabove; and the pharmaceutically acceptable salts thereof.

The alkyl moiety present in the $R^1$ group which links the cycloalkyl, cycloalkenyl, aryl, or furan-2-yl moiety to the basic nitrogen atom in the compounds of formulas I, II or III is a lower(alkyl) group, preferably $-(CH_2)_n-$, wherein n is about 1-5, most preferably n is 1, e.g., $R^1$ is $C_3-C_6$(cycloalkyl)methyl, $C_5-C_7$(cycloalkenyl)methyl, arylmethyl or furan-2-ylmethyl. Preferred aryl moieties include $(C_6-C_{10})$aryl, i.e., phenyl, benzyl, tolyl, xylyl, anisyl and the like.

In formulas I, II or III, the position of the $-R^4$ and $-R^5$ groups indicate that they can be either ortho, meta, or para to the $-X$ group or the $-N=$ group, respectively, e.g., $R^4$ and/or $R^5$ can occupy any available site on the phenyl ring. In structure I, II and III, a bond designated by a wedged or darkened line indicates one extending above the plane of the phenyl rings. A bond designated by a broken line indicates one extending below the plane of the phenyl rings.

These delta-opioid antagonists include compounds of the formula I, formula II or formula III, wherein $R^1$ is $(C_1-C_5)$alkyl, $C_3-C_6$(cycloalkyl)alkyl or $C_5-C_7$(cycloalkenyl)alkyl, preferably wherein $R^1$ is $(C_2-C_3)$alkyl or $C_3-C_6$(cycloalkyl)methyl, and most preferably wherein $R^1$ is cyclopropylmethyl. $R^2$ is preferably OH or OAc ($O_2CCH_3$), and $R^3$ preferably is H. Preferably, at least one, and most preferably, both of $R^4$ and $R^5$ are H, or $R^4$ is H and $R^5$ is NCS, i.e., 5′-NCS. Preferred compounds also result when $R^4$ is H and $R^5$ is F, $(C_1-C_5)$alkyl or $(C_1-C_5)$alkoxy.

The compounds of formulas I, II and III are selective for the δ opioid receptor. Particularly, the compounds of formula II are specific for the $δ_1$ subset of delta receptors. The delta selectivity of compounds of formulas I, II or III is apparently the salient characteristic of these compounds that inhibits the reinforcing properties of cocaine or inhibits dependence or addiction to cocaine. As used herein, the term "inhibit" encompassses 100% inhibition, or blockage of cocaine use, as well as amounts of cocaine inhibition which are clinically significant. The compounds of formulas I, II and III can also be used as pharmacological and biochemical probes of opiate receptor structure and function, e.g., to measure the selectivity or lack thereof of other known or suspected opioid receptor antagonists or agonists.

Since the compounds of the invention are formally morphinan derivatives, it is believed that their ability to cross the "blood-brain barrier" and to affect the CNS should be far superior to peptide delta opioid antagonists.

Most of the extant knowledge about cocaine's ability to reinforce its own use centers around the neurotransmitter dopamine. For example, several studies have shown that cocaine binds to the dopamine transporter and inhibits dopamine reuptake. (M. J. Kuban et al., in "Mechanisms of Cocaine Abuse and Toxicity," D. Clovet et al., eds., NIPA Research Monography, (1988) at pages 14–22. This theory, by itself, does not predict that an opioid antagonist, particularly a specific delta-opioid antagonist, would modify cocaine's ability to be reinforcing. In fact, inasmuch as the concepts involving dopamine are a reasonably complete account of cocaine's salient effects, the concepts argue against delta-opioid involvement in cocaine addiction. Other data argue against the idea of delta-specific-opioid involvement in heroin addiction. Thus, from the perspective of extant theory, there is no logical reason to predict that delta-specific antagonists would be useful for treating cocaine abuse.

Although exemplified with reference to cocaine, the method of the present invention is also effective with bioactive cocaine analogs, some of which are many times more potent than cocaine. Such analogs include cocaethylene and those disclosed by A. P. Kozikowski et al., Med. Chem. Res., 1, 312 (1991), by F. I. Carroll et al., J. Med. Chem., 35, 969 (1992), and R. L. Clark et al., J. Med. Chem., 16, 1620 (1973), including 3β-phenyltropane-2β-carboxylic acid methyl ester and 3β-(p-fluorophenyl)tropane-2β-carboxylic acid methyl ether. As used herein, the term "cocaine" includes R-cocaine and the pharmaceutically acceptable salts thereof, which include salts of organic and inorganic acids, e.g., the sulfate, lactate, nitrate, phthalate pentahydrate, tartrate trihydrate, citrate, valerate, hydrobromide, hydrochloride, methylbromide, malate and oleate salts.

A further aspect of the present invention comprises an article of manufacture or kit comprising packaging material, such as a carton, envelope, bottle, vial, blister pack, intravenous bag and the like, and at least one pharmaceutical unit dosage form, such as a tablet or capsule, comprising an amount of a compound of formula I, II, III or a mixture thereof, effective to treat human cocaine use or addiction; and wherein said packaging material comprises instruction means therein or thereon, such as a printed label, package insert, tag, cassette tape, video-tape and the like, which indicates that said unit dosage form can be used to treat (reduce or block) human cocaine use, or addiction due to the administration of cocaine to a human.

Although exemplified and embodied primarily with reference to cocaine, a further embodiment of the invention comprises administration of one or more of the compounds of formulas I, II or III in an amount effective to treat abuse of, or addiction to, other central (CNS) psychomotor stimulants, such as phenylisopropylamine (amphetamine) or phenylisopropylamine derivatives, such as those disclosed by R. A. Glennon et al. in Psychopharmacology: The Third Generation of Progress, H. Y. Meltzer, ed., Raven Press, New York (1987) at pages 1627–1634 and by D. P. Van Kammen et al. in Handbook of Stereoisomers: Drugs in Pharmacology, D. F. Smith, ed., CRC Press, Boca Raton, Fla. (1984) at pages 297–315. Such derivatives include 2-amino-3-[(2'-,3'- or 4'-methoxy)phenyl]propane (OMA, MMA and PMA, respectively), 2-amino-3-[3',4'-dimethoxyphenyl]propane (3,4-DMA); 2-amino-3-[2',4'-dimethoxyphenyl]propane; 2-amino-3-[3',4'-dimethoxyphenyl]propane (3,4-DMA); 2-amino-3-(2',4'- or 2',5'-dimethoxyphenyl)propane; 2-amino-3-[(2',4',5'-,2',4',6'-, or 3',4',5'-trimethoxy)phenyl]propane; N-methylamphetamine, N,N-dimethylamphetamine, N-ethylamphetamine, N-propylamphetamine, 2-amino-2-methyl-3-phenylpropane, ephedrine, norephedrine, cathinone ("khat"), norpseudoephedrine, 3,4-methylenedioxyphenylisopropylamine (3,4-MDA or MDA), N-monomethyl-3,4-methylenedioxyphenylisopropylamine (MDMA, "Ecstasy"), and N-monoethyl-3,4-methylenedioxyphenylisopropylamine (MDEA; "Eve"), including the R- and S- isomers or racemic mixtures thereof. Thus, kits equivalent to those disclosed above which are assembled with instruction means to treat amphetamine, MDMA or other phenylisopropylamine psychomotor central stimulant abuse are also within the scope of the invention.

BRIEF DESCRIPTION OF THE FIGURES

FIG. 2 corresponds to FIG. 1 in K. Menkens et al., Eur. J. Pharmacol., 219, 345 (1992).

FIG. 3 corresponds to FIG. 1A in L. D. Reid et al., Life Sciences, 52, 67 (1993).

DETAILED DESCRIPTION OF THE INVENTION

Chemistry

Figure 1:
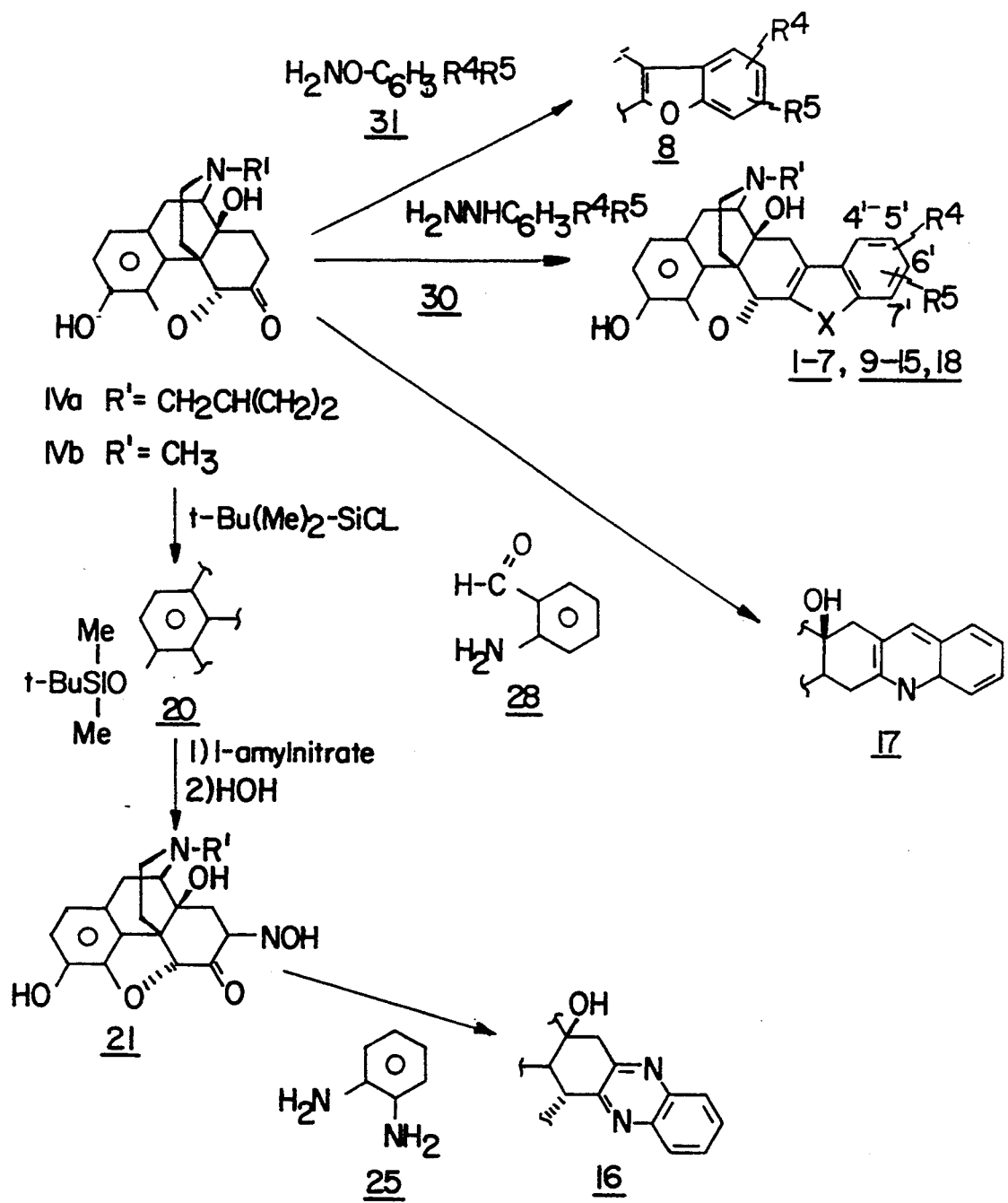
FIG. 1 is a schematic depiction of the synthesis of compounds of formula I and formula III.

Representative compounds of formula I (1–15 and 18) or formula III (16–17) were synthesized from starting materials of formula IVa or IVb as outlined in FIG. 1, as described in U.S. Pat. No. 4,816,586. The structures of compounds 1–15 and 18, shown generally in FIG. 1, are summarized on Table I, below.

TABLE I*

[Structure: morphinan with N—R¹, OH, positions showing C-ring with 6,7-positions, X, R⁴, R⁵, HO- group]

| Compound No. of Table I | R¹ | X | | R⁴ |
|---|---|---|---|---|
| 1 | CpCH₂[1] | NH | H | H |
| 2 | CpCH₂ | NCH₃[2] | H | H |
| 3 | CpCH₂ | NH | H | 5'-F |
| 4 | CpCH₂ | NH | H | 5'-OCH₃ |
| 5 | CpCH₂ | NH | H | 5'-CH₃ |
| 6 | CpCH₂ | NH | H | 5'-NO₂ |
| 7 | CH₃ | NH | H | H |
| 8 | CpCH₂ | O | H | H |
| 9[3] | CpCH₂ | NH | H | 5'-OH |
| 10 | CpCH₂ | NH | H | 4'-F |
| 11 | CpCH₂ | NH | H | 7'-F |
| 12 | CpCH₂ | NH | H | 4' and 6'-CH₃ (mixture) |
| 12a | CpCH₂ | NH | H | 5'-NH₂ |
| 12b | CpCH₂ | NH | H | 5'-NCS |
| 13 | CpCH₂ | NH | H | 7'-CH₃ |
| 14 | CpCH₂ | NH | H | 7'-OCH₃ |
| 15[4] | CpCH₂ | NH | H | 7'-OH |
| 18 | CpCH₂ | NH | 6'-CH=CH—CH=CH-7' | |

[1]Cyclopropylmethyl.
[2]From Fischer indole synthesis of IVa + H₂NN(CH₃)Ph.
[3]Derived from 4 using five equivalents of BBr₃.
[4]Hydrolysis product formed during synthesis of 14.
*From Portoghese et al. (U.S. Pat. No. 4,816,586).

Compounds 1–18 have either indole (1–7, 9–15), benzofuran (8), benzopyrazine (16), benzoquinoline (17) or benzoindole (18) moieties, fused to the 6,7-position of the opiate C-ring.

Starting Materials

The structures, common names and Merck Index reference numbers of representative 4,5-epoxy-6-ketomorphinan starting materials of general formula IV are summarized on Table II, below.

TABLE II*

[Structure IV: morphinan with N—R¹, R¹, R¹O-, O, and ketone]

| Compound | R¹ | R² | R³ | Common Name | Merck No.[2] |
|---|---|---|---|---|---|
| IVa | CH₂CH(CH₂)₂ | OH | H | naltrexone | 6209 |
| IVb | CH₃ | OH | H | oxymorphone | 6837 |
| IVc | CH₃ | H | H | hydromorphone | 4714 |
| IVd | CH₃ | H | CH₃ | hydrocodone | 4687 |
| IVe[1] | CH₂CH(CH₂)₂ | H | H | — | — |
| IVf | CH₂CH=CH₂ | OH | H | naloxone | 6208 |
| IVg | CH₃ | OH | CH₃ | oxycodone | 6827 |

[1]Preparation, M. Gates et al., J. Med. Chem., 7, 127 (1964).
[2]The Merck Index, W. Windholz, ed., Merck & Co., Rahway, NJ (10th ed. 1983).
*Portoghese et al. (U.S. Pat. No. 4,816,586).

Other starting materials of formula IV can be prepared by synthetic methods which are well known in the art of organic chemistry. For example, compounds of formula IV wherein R¹ is H and R³ is a suitable protecting group, and wherein the 6-keto group has also been protected, can be prepared from compounds IVa-q. These intermediates can be N-alkylated and deprotected to yield compounds of formula I wherein R¹ is C₂–C₅(alkyl), C₄–C₆(cycloalkyl)alkyl, C₅–C₇(cycloalkenyl)alkyl, aryl, aralkyl, trans-C₄–C₅-alkenyl or furan-2-ylalkyl, by the application of well known reactions.

For example, the free hydroxyl groups of compounds of formula IV, e.g., R²=OH and/or R³=H, can be protected by acid-labile groups such as tetrahydropyranl-yl, trimethylsilyl, 1-methoxy-isopropyl and the like as disclosed in *Compendium of Organic Synthetic Methods*, I. T. Harrison et al., eds., Wiley-Interscience, New York, NY (1971) at pages 124–131, (hereinafter "Compendium"), the disclosure of which is incorporated by reference herein. The protection of the 6-keto group of compounds of formula IV by its reversible conversion into a ketal or a thioketal group is disclosed in *Compendium*, at pages 449–453, the disclosure of which is incorporated by reference herein. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955), the disclosures of which are incorporated by reference herein.

Procedures for the alkylation of secondary amines with halides under basic or neutral conditions are well known. For example, see *Compendium* at pages 242–245; *Org. Synth.*, 43, 45 (1963); *J. Org. Chem.*, 27, 3639 (1962) and *J. Amer. Chem. Soc.*, 82, 6163 (1960), the disclosures of which are incorporated by reference herein.

Compounds of formulas I, II or III wherein R² is acyloxy and/or R³ is acyl can be prepared by using the corresponding starting material IV. For example, starting material IVa can be diacylated by reacting it with the appropriate (C₁–C₅)alkyl anhydride in pyridine for 10–18 hrs at 18°–25° C. The resultant 3,14-diacylated compound can be converted to the 14-acylated compound by limited hydrolysis. The 3-acylated starting materials can be prepared by the short-term reaction of the compound of formula IV with the anhydride, e.g., for about 2–4 hours. The 3-acylated product can be separated from the 3,14-diacylated product by chromatography.

Synthesis of Delta Opioid Receptor Antagonists

The preparation of 1–7, 9–15 and 18 was accomplished using the Fischer indole synthesis. See R. B. Van Orden et al., *Chem. Rev.*, 30, 78 (1942), the disclosure of which is incorporated by reference herein. A compound of formula IV, e.g., naltrexone hydrochloride (IVa.HCl) or oxymorphone hydrochloride (IVb.HCl) and the appropriate aromatic hydrazine hydrochloride (30) were refluxed in glacial acetic acid or methanol containing an organic or inorganic acid such as methanesulfonic acid or hydrochloric acid (HCl) for 3–6 hours. Compound 12b was prepared by reducing 5'-nitroindole (6) to the 5'-amino derivative 12a, which was treated with thiophosgene to yield 12b, as the hydrated salt. See P. S. Portoghese et al., *J. Med. Chem.*, 31, 281 (1988). The 6',7'-benzo-derivative (18), was prepared by refluxing naltrexone.HCl with 1-napthylhydrazine.

Benzofuran 8 was prepared by refluxing an ethanol solution containing equivalent amounts of IVa.HCl, methane sulfonic acid and o-phenylhydroxylamine.HCl (31) for 18 hours.

The benzopyrazine 16 was synthesized from IVa.HCl by a conversion to the oximino derivative 21 followed by reaction with o-phenylenediamine 25.

The quinoline derivative 17 was prepared by refluxing naltrexone.HCl with o-aminobenzaldehyde 28 and methanesulfonic acid in ethanol. The corresponding benzothiophene derivatives (I, X=S) can be synthesized by reacting a compound of formula IV with thiophenol in the presence of an acid, followed by photolysis of the OH-protected thioenol under a nitrogen atmosphere using a Hg high pressure lamp (see S. H. Green et al., *J. Org. Chem.*, 33, 2218 (1968), the disclosure of which is incorporated by reference herein).

The acid salts of compounds of formulas I, II, or III, wherein $R^3$=H can be converted into the corresponding $(C_1-C_5)$alkoxy derivatives $[R^3=(C_1-C_5)alkyl]$ by dissolving the starting material in DMF and adding an excess of the appropriate $(C_1-C_5)$alkyl iodide and an amine such as diisopropylethylamine. The reaction can be conducted at an elevated temperature for about 4–10 hours. The final product can be purified by column chromatography.

Pharmaceutically acceptable amine salts of these compounds may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. These physiologically acceptable salts are prepared by methods known in the art, e.g., by dissolving the free amine bases with an excess of the acid in aqueous alcohol.

The synthesis of compounds 1–12 and 13–17 is set forth in detail in P. S. Portoghese (U.S. Pat. No. 4,816,586), the disclosure of which is incorporated by reference herein.

The compounds of formula II can be readily synthesized by reacting a compound of formula IV with benzaldehyde or a mono- or di-substituted derivative thereof in the presence of base, as shown below.

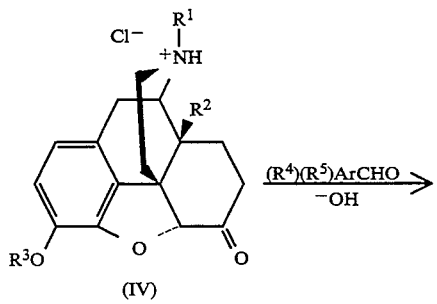

(IV)

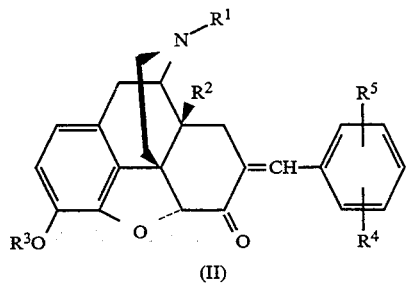

(II)

wherein $R^1$, $R^2$, $R^3$, $R^4$ and $R^5$ are as disclosed hereinabove. Preferably, IV is naltrexone hydrochloride, e.g., $R^3$=H, $R^2$=OH and $R^1$ is cyclopropylmethyl, and the synthesis of compound II wherein $R^2$=OH, $R^1$=cyclopropylmethyl and $R^3$=$R^4$=$R^5$=H is carried out as described by P. S. Portoghese et al., *J. Med. Chem.*, 34, 1292 (1991). When $OR^3$ and/or $R^2$ are base-liable groups such as alkanoxy, $R^3$ may be H and $R^2$ may be OH in the compound of formula II. In such situations, the protecting groups can be replaced by art-recognized methodologies for the protection/deprotection of hydroxyl groups. Of course, if naltrexone.HCl or a similar compound of formula IV, comprising free OH groups is used to prepare compounds of formula II wherein $R^3$ is H and/or $R^2$ is OH or H, the free hydroxyl groups in the compound of formula II can be also converted to alkanoyloxy groups by methods known to the art.

The synthesis of specific embodiments of the compounds of formula II is set forth in detail in U.S. patent application Ser. No. 07/867,997, filed Apr. 13, 1992.

Administration and Dosage Forms

In the clinical practice of the present method, the compounds of the present invention will normally be administered orally or parenterally, as by injection or infusion, in the form of a pharmaceutical preparation comprising the active ingredient in combination with a pharmaceutically acceptable carrier, e.g., in the form of a pharmaceutical unit dosage form. The carrier may be a solid, semi-solid or liquid diluent or be compressed or shaped into an ingestible capsule. The compound or its salt may also be used without carrier material.

Examples of pharmaceutical unit dosage forms comprising the present antagonists include tablets, preselected volumes of intravenous solutions, suspensions, hard or soft gelatin capsules, microcapsules, suppositories, liposomes and systems designed for controlled or prolonged release of the active agent, such as reservoirs designed for transdermal delivery or subcutaneous delivery. Such reservoirs include skin patches and shaped polymeric implants. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

Doses of a given compound of formulas I, II or III which are effective to counteract the use of cocaine, including cocaine salts or analogs can be extrapolated, to some extent, from the murine data disclosed hereinbelow, by methods known to the art for extrapolation of animal dosing data to humans. For example, see U.S. Pat. Nos. 5,035,878 and 4,938,949.

Bioassays

There are a number of germane bioassays. These include (a) tests using guinea pig ileal longitudinal muscle (GPI), (b) tests using mouse vas deferens (MVD), and those indexing behavior of mice or rats which include, (c) writhing associated with injections of irritants, (d) conditioned place preference (CPP) tests, (e) tests using rewarding brain stimulation and (f) drug self-administration tests. Each of these methods are widely used by practitioners of the art, because information derived from these bioassays predict responsiveness in human beings. Each assay is briefly described.

A. Tests Using Guinea Pig Ileal Muscle

When the extracted longitudinal muscle from the guinea pig ileum (GPI) is suspended in a physiological medium, electrical stimulation reliably produces contractions. Responsiveness to the electrical stimulation, therefore, can be used to index the effects of drugs. The procedures used and common results have become standard, as exemplified by the observations that morphine reliably suppresses the contractions that would ordinarily follow from the electrical stimulation and classic opioid antagonists, such as naloxone and naltrexone, block morphine's effects.

B. Mouse Vas Deferens (MVD)

The mouse vas deferens is sensitive to delta-opioid drugs. Furthermore, the MVD responds selectively to delta opioids. It is, therefore, useful in indexing selective delta-opioid drugs. The methods used here are described by Henderson et al. (*Brit. J. Pharmacol.*, 46, 764 (1972)), the disclosure of which is incorporated by reference herein.

C. Writhing as an Index of Pain and Analgesia of Drugs

When mice are injected with an irritant, they respond by a characteristic writhing that can be inhibited by analgesics. Consequently, the writhing response can be used to index the effects of particular opioids. The methods are standard and the particular methods used here are described by G. Hayashi et al. (*Eur. J. Pharmacol.*, 16, 63 (1971)).

D. Conditioned Place Preference (CPP) Testing

Testing associated with conditioning place preference (CPP) procedures involves some rather straightforward assumptions and observations. It is assumed, for example, that subjects (a) will return to places in which they experience something akin to pleasure, (b) will avoid places in which they experience an aversive state, and (c) will be neutral toward places in which they experience an affective state that is neutral or in which no discernable change in affective state has occurred. Drugs can produce states that are pleasurable, aversive, or have no particular affective consequences. It follows, from these simple assumptions, that rats might spend more time in places where they experienced a drug-induced pleasurable effect, less time in places in which they experienced a drug-induced aversive state and be neutral toward places in which they experienced no particular change in affective state.

The assumptions that subjects react predictably with respect to experimenter-induced changes in affective states is confirmed by extensive observations. J. Garcia et al. (*Brit. J. Radiology*, 30, 318 (1957)), for example, demonstrated that rats avoided a place which had been paired with radiation sufficient to induce illness. H. D. Beach (*Can. J. Psychol.*, 11, 104 (1957)) found that rats would go to places where they had previously experienced the effects of morphine.

L. D. Reid (N. A. Rossi and L. D. Reid, Affective States Associated with Morphine Injections (*Physiol. Psychol.*, 4, 269–274 (1976)) performed an experiment that was directed toward germane issues. One issue was whether or not the state produced by drugs such as morphine which, in turn, increased pressing for direct electrical stimulation of brain produced a state that was, in turn, capable of establishing a place preference. If the doses of morphine that facilitated pressing for brain stimulation were also the doses of morphine that would condition a place preference, then it would be reasonable to conclude that those doses produced a positive affective state.

To devise a procedure as a test of the pleasure-producing effects of drugs, an alley was built. One side of this alley was clearly discriminable, by rats, from the other side of the alley. One side of the alley could be separated from the other side by a door. With the door open and with the rats having access to the entire alley, testing was done to determine whether or not a rat preferred one side of the alley over the other, i.e., baseline preferences were determined.

After baseline preferences were determined, selected doses of morphine were given to rats in one side of an alley, i.e., rats, under the influence of morphine, were put into only one side of the alley with doors closed and without access to the other side. On the next day, doses of placebos were given before a rat was placed in the other side. This procedure was repeated across a number of days. On a test day and subsequent to conditioning, rats were again allowed access to the entire alley (without injections of either drug or placebo).

It was found that a dose of morphine that rats are apt to self-administer and that facilitated pressing for rewarding brain stimulation caused rats to spend more time in the place of the experience of that drug. In other words, rats had a preference for the place of the experience of morphine. This study demonstrated that the drug-induced facilitated pressing for brain stimulation reflected a rewarding, positive affective event.

Thus, a procedure had been developed that could be used to assess the affective states produced by other drugs. After further testing of the test itself, place preference testing has become the most widely used procedure to resolve questions about whether or not a drug produces an affective state. The procedure has come to be known as the conditioned place preference paradigm or conditioned place preference (CPP) test (C. D. Carr et al., *The Neuropharmacological Basis of Reward*, S. Liebman et al., eds., Oxford U. Press, New York, 1989, at pages 264–319).

Drugs that are abused by people produce CPPs among rats. Cocaine, for example, establishes a CPP. Other addictive psychomotor stimulants also can establish CPPs. Psychoactive drugs that are not readily taken by people do not produce positive CPPs. Drugs producing signs of illness produce place aversions. With extensive experience with testing with rats and drugs that are addictive among people, it is found that addictive drugs are self-administered by a wide variety of laboratory animals and they produce CPPs among rats.

As the study of addictive drugs has progressed, the consensus was reached that these drugs' salient effects could be indexed by (a) the readiness with which rats self-administered them, and (b) whether or not doses of the drugs would establish a place preference, indicating that the subjects experienced a pleasant state under the influence of the drug, i.e., whether a drug produced a positive CPP. Also, as theory and practice of the study of addictive drugs among laboratory animals progressed, another test has become accepted as a reliable and valid index of the addictive properties of drugs, the test associated with pressing for direct electrical stimulation of brain.

E. Pressing for Rewarding Brain Stimulation

Although one can have considerable confidence that tests using conditioned place preference procedures are reasonable models (a) for assessing the reinforcing effects of drugs, and (b) for assessing the kind of drug that might antagonize those reinforcing effects, one could more confidently conclude that a particular drug will block the reinforcing effects of cocaine, if the conclusion was supported by a different kind of test. In other words, there would be more confidence in a conclusion drawn from one set of procedures, if a set of converging operations (i.e., other procedures) provided support for the derived conclusion. As discussed below, tests involving pressing for rewarding brain stimulation are another class of procedure for assessing a drug to see if it blocks the salient effects of cocaine. Consequently, additional support for the concept that the present delta-specific opioid antagonists will be valuable agents for treating cocaine and phenylisopropylamine stimulant abuse is provided by tests involving rewarding brain stimulation.

Extant theory is that cocaine achieves its reinforcing properties by blocking reuptake of dopamine associated with the activity of the medial forebrain bundle system. The medial forebrain bundle system (particularly the mesolimbic dopamine component of that system) is thought to be the central neural system whose activity is manifest as positive affect. Positive affect is a concept similar to the concepts of positive mood, euphoria, pleasure, positive incentive, and reward. Each concept is used technically from slightly different perspectives, but each refers to similar phenomena. When an increment in positive affect is a consequence of an act, that increment reinforces the act (i.e., increases the probability of the act's reoccurrence) and positive reinforcement is said to occur. Stated slightly differently, cocaine's effects reinforce the act of taking cocaine by modifying affective state so that it is more positive than previously discerned. The increase toward positive affect, in turn, is a product of cocaine's ability to block reuptake of dopamine within the medial forebrain system, the system whose activity is positive affect.

The conclusion that the medial forebrain bundle is the neural structure most salient to the manifestation of positive affect is derived from a long series of investigations showing that direct electrical stimulation of the medial forebrain bundle, by way of chronically indwelling electrodes in freely moving rats, produces effects that are clearly reinforcing. Furthermore, direct electrical stimulation of the medial forebrain bundle controls behavior in the same way as delivery of more conventional reinforcers (L. D. Reid, "Tests involving pressing for intracranial stimulation as an early procedure for screening likelihood of addiction to opioids and other drugs," in M. A. Bozarth, ed., *Methods of Assessing the Reinforcing Properties of Abused Drugs*, Springer-Verlag, New York (1987) at pages 391–420.)

Addictive drugs, such as cocaine and morphine, increase pressing for brain stimulation of the medial forebrain bundle, provided doses of the addictive drugs are similar to those that might be self-administered. Further, those agents that increase pressing for rewarding brain stimulation also, at the same doses and times after dosing, produce conditioned place preferences (Rossi & Reid, cited above).

The consensus is, therefore, that drug-induced changes in rates of pressing for brain stimulation reflect the addictive properties of drugs. An agent blocking cocaine's reinforcing effects would, therefore, in turn, block cocaine's ability to increase pressing for brain stimulation. Further, if the agent is relatively specific to blocking cocaine's effects, rather than merely blocking all affective or motor responses, then the agent should not also produce a disruption of the rat's basic ability to press.

Drug Self-Administration Testing

When rats are fixed with chronically indwelling intravenous catheters, drugs can be administered as the rats are walking around. These same rats can be put into a box equipped with a lever, the depression of which actuates a pump that can deliver drug through the catheter, i.e., the rats can be put into a Skinner box with drug administration a contingency of lever-pressing. Standard procedures have been developed to study the propensity of rats to self-adminster drugs and these procedures are called drug self-administration procedures or tests. See J. R. Weeks et al., "Screening for Drug Reinforcement Using Intravenous Self-Administration in the Rat," Bozarth, cited above, at pages 35–44.

EXAMPLE 1

Evaluation of Antagonist Activity

A. Materials and Methods

1. Guinea Pig Ileal Longitudinal Muscle (GPI). Ilea from guinea pigs were taken approximately 10 cm from the ileocaecal junction, and a strip of longitudinal muscle with the myenteric plexus attached was prepared by method of Rang et al., *Brit. J. Pharmacol.*, 22, 356 (1964), the disclosure of which is incorporated by reference herein. A 1 cm portion of this strip was then mounted between two platinum electrodes placed in a 10 ml organ bath and connected to an isometric transducer. Contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 $\mu$M chlorpheniramine maleate was the bathing solution and was continuously bubbled with 95% $O_2$ and 5% $CO_2$. The organ bath was maintained at 36°–37° C. The longitudinal muscle strip was allowed to equilibrate with continuous stimulation for a minimum of 90 min. Cumulative concentration-response curves were determined after drugs were added to the bath in 10- to 50-$\mu$L amounts and washed out with two 10 ml portions of buffer after noting their maximum effects.

2. Mouse Vas Deferens (MVD). This assay was performed according to the description by Henderson et al., *Brit. J. Pharmacol.*, 46, 764 (1972), the disclosure of which is incorporated by reference herein. Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10- to 50-$\mu$L amounts and washed out after noting their maximum effect.

B. Pharmacology

The compounds were tested in vitro on the mouse vas deferens (MVD) and guinea pig ileum (GPI) preparations. Each compound (100 or 200 nM) was incubated for 15 min with the tissue prior to adding graded doses of a standard agonist for determination of an $IC_{50}$ value. The standard agonists employed were [D-Ala$^2$, D-Leu$^5$-]enkephalin (DADLE), morphine (M), and ethylketazocine (EK); these are selective for delta, mu, and kappa opioid receptors, respectively. The $IC_{50}$ value was divided by the control $IC_{50}$ value in the same tissue, and this $IC_{50}$ ratio (DR) was employed to calculate the Ke value using the equation Ke=[antagonist]/(DR-1). The results of these bioassays are summarized on Table III, below.

TABLE III*

In Vitro Antagonist Activity of 6,7-Dehydro-3,14-dihydroxy-4, 5α-epoxymorphinan Derivatives

| Compound No. | $K_e$ (nM)[a] DADLE[b] | M[c] | EK[d] |
|---|---|---|---|
| 1  | 0.22  | 29.4  | 45.5 |
| 2  | 1.5   | 12.5  | 22.2 |
| 3  | 2.0   | 61.7  | 46.2 |
| 4  | 5.7   | 63.0  | 12.6 |
| 5  | 4.2   | >160  | >250 |
| 6  | 168.0 | 92.0  | ≧200 |
| 7  | e     | e     | e    |
| 8  | 1.8   | 30.8  | 50.8 |
| 9  | —     | 27.2  | 68.5 |
| 10 | 5.5   | >125  | >170 |
| 11 | 0.35  | 5.3   | >330 |
| 12 | 4.8   | >125  | >143 |
| 13 | 1.5   | 19.1  | >330 |
| 14 | 6.6   | 35    | —    |
| 16 | 1.4   | 6.1   | 13.4 |
| 17 | 2.7   | 11.3  | 16.3 |

[a] $K_e$ = [antagonist]/(IC$_{50}$ ratio − 1), where the IC$_{50}$ ratio represents the response of the tissue to an agonist in the presence of the antagonist divided by the control IC$_{50}$ of the agonist in the same tissue.
[b] [D-Ala$^2$, D-Leu$^5$]enkephalin in the mouse vas deferens preparation (MVD).
[c] Morphine in the guinea pig ileum preparation (GPI).
[d] Ethylketazocine in the GPI.
[e] No agonist antagonism observed.
*From Portoghese et al. (U.S. Pat. No. 4,816,586).

All of the N-cyclopropylmethyl compounds (1-6, 8-14 and 16-17 antagonized the effect of the delta agonist, DADLE. Substantially less antagonism toward morphine and EK was observed. These compounds were devoid of agonist activity or behaved as weak, partial agonists, with dose-response curves that plateaued at 20-40% of the maximal response at a concentration of 1 μM. The agonist effect was consistently below 20% at the concentrations employed (20-200 nM) for antagonist testing.

The N-methyl compound 7 also exhibited partial agonist activity. However, because its agonist effect was below 20% only at 5 nM or less, it was tested for antagonist activity at this concentration and was found to be inactive in this regard.

EXAMPLE 2

Antagonist Activity of NTI In Vivo

The highly active delta antagonist NTI (1) of the series was evaluated in mice for its effectiveness in antagonizing the antinociceptive effect of Tyr-D-Ser-Gly-Phe-Leu-Thr (DSLET), morphine, and U50488H. These agonists were employed because their agonist activity is selectively mediated through delta, mu, and kappa opioid receptors, respectively.

TABLE IV*

| In Vivo Antagonist Activity of NTI (1) in Mice* | |
|---|---|
| Agonist | ED$_{50}$ Ratio[a] |
| DSLET[b] | 5.25 (2.70-11.11) |
| Morphine[c] | 1.15 (0.54-2.78) |
| U50488H[c] | 1.23 (0.63-2.86) |

*Methodology of G. Hayashi et al., Eur. J. Pharmacol., 16, 63 (1971).
[a] ED$_{50}$ value of treated mice (20 mg/kg s.c.) divided by ED$_{50}$ of control mice.
[b] Administered intracerebroventicularly (i.c.v.).
[c] Administered subcutaneously (s.c.).
*From Portoghese et al. (U.S. Pat. No. 4,816,586).

As shown by the data on Table IV, compound 1 at 20 mg/kg s.c. effectively blocked the writhing inhibition due to DSLET (ED$_{50}$ ratio=5) without significantly antagonizing the effect of morphine or U50488H.

Therefore, both the in vitro and in vivo data show that fusion of the indole, benzofuran, benzopyrazine or quinoline ring system to the C-ring of naltrexone gives rise to compounds that possess a unique opioid receptor antagonist profile. Most of these compounds are highly selective for the delta opioid receptor, and the unsubstituted indole 1 appears to be an order of magnitude more potent than its substituted congeners. The selectivity ratios of NTI are approximately 50 for delta/mu, and possibly greater for delta/kappa.

It can be noted that the benzofuran 8, while less potent and less selective than 1 as a delta antagonist, nevertheless retains substantial delta antagonist activity. A similar relationship was observed with the benzopyrazine 16 and the quinoline 17. This indicates that the indole ring system is not necessary for delta selectivity. Possibly, the role of the pyrrole, furan, pyrazine and quinoline moieties in these compounds is to restrain the additional benzene ring so that it is a coplanar to the C-ring of the morphinan nucleus.

EXAMPLE 3

NTI's Effects Block Cocaine's Ability to Establish a Conditioned Place Preference To test NTI's ability to block cocaine's ability to establish a CPP, male, Lewis rats were subjected to standard procedures associated with testing for place preferences. The rats were first habituated to being handled.

Then, the rats were put into an alley having two distinctive sides with the barrier separating the two sides not in place, i.e., a baseline preference for the two sides was measured. After baseline was determined, the conditioning procedures began.

The conditioning procedures were the same for all rats, except that there were four different regimens of drug administration, one regimen for each of four different groups of rats (12 rats a group). The conditioning procedure involved one set of kind of injections before a rat was placed in one side of the alley and another set of kind of injections before being placed in the other side.

The group of rats that received the procedures usually used to show a cocaine-produced CPP, received cocaine-injections (plus a placebo injection) before being put into the putative side of conditioning. The dose of cocaine was 15 mg/kg given subcutaneously, a relatively large dose of cocaine. On the next day, this group received placebo injections before being put into the alternative side. These procedures were repeated throughout conditioning. On test day, with the rats having access to both sides of the alley, it would be expected that these rats would favor (compared to their baseline scores) the place of the experience of cocaine (i.e., the side of putative conditioning). That was the case for this standard group of cocaine-CPP.

There was also a group that received placebos (vehicles for both cocaine and NTI) before being placed in either side of the chamber. This is a typical control group and can be used to determine if merely the procedures themselves of handling the rats leads rats to change their preference for a side of the alley. The rats merely receiving placebo injections did not significantly change their preference for a side of the alley.

There was yet another control group. This group received NTI before being placed in the side of putative conditioning and placebos at other times. This group's preference did not significantly change from baseline to testing. So, the basic conditions for testing a NTI's effects on cocaine's ability to establish a CPP indicative of cocaine's positivity were set. Cocaine (with appropriate placebo injections) established a positive CPP. Injections of NTI and injections of placebos did not significantly modify rats' preferences for the side of an alley.

Figure 2:
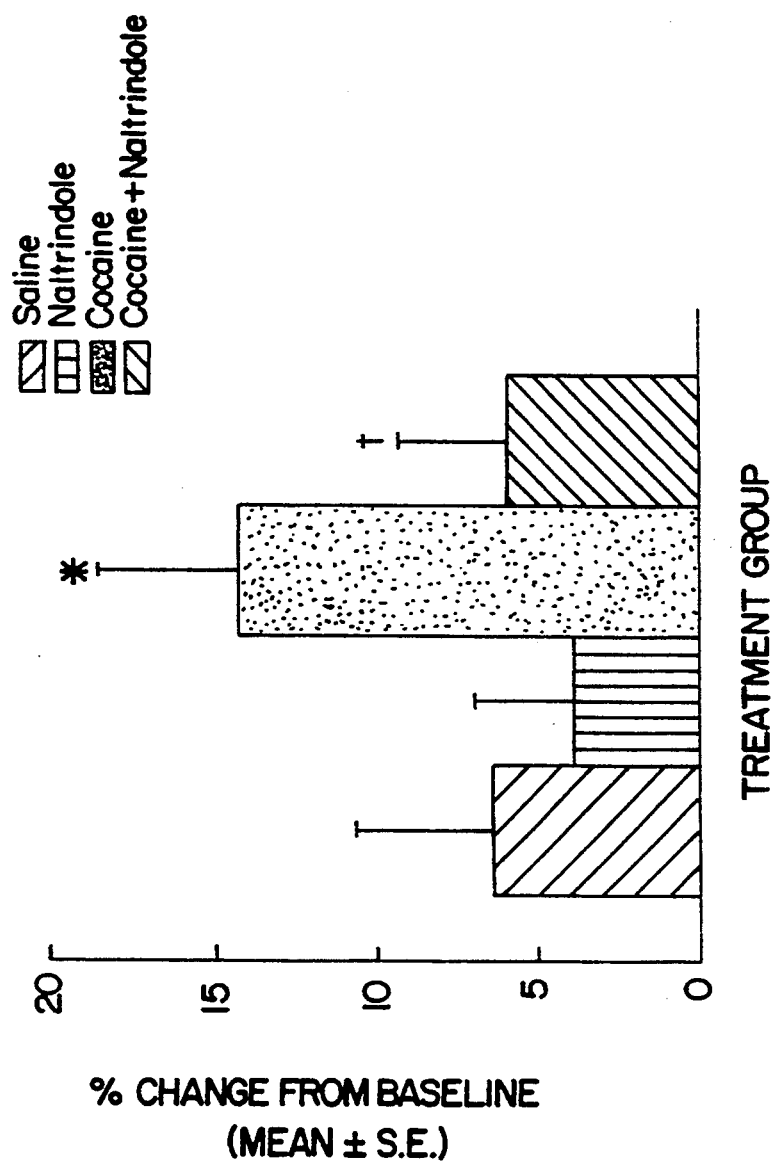
FIG. 2 is a graph depicting the effect of saline, NTI, cocaine and cocaine+NTI on conditioned place preference in rats. Cocaine produced a significant (asterisk) positive place preference which was antagonized by naltrindole (dagger).

FIG. 2 depicts the mean percent change from baseline for each of the experimental groups. The group represented by the open bar (far left bar) received only injections of placebos before being put into either side of the apparatus, i.e., this is a placebo control group. The scores at testing did not differ statistically from baseline scores for this control group. The striped bar depicts the mean scores of the group that received NTI before being placed into the side of conditioning and saline before being placed into the other side. The scores of this group are not statistically different at testing from baseline. The solid black bar depicts the scores of the group getting cocaine before being put into the side of conditioning (saline or placebo before being put into the other side). This group was subjected to the standard procedure for demonstrating a positive cocaine conditioned place preference. The cocaine-CPP group's test score is statistically significantly different than its baseline score and is significantly larger than the placebo-control group's scores, i.e., a cocaine CPP was established. The cross-hatched bar depicts the mean score of the group treated with cocaine but also receiving NTI. This cocaine-NTI group scores are significantly different from the cocaine group's scores but not different from the other groups' scores. When NTI (3 mg/kg, interperitoneally) was given before injections of cocaine and a group of rats were treated exactly as those given placebo before injections of cocaine, there was a marked difference in outcomes between the two groups. As mentioned, rats without NTI showed a preference for the place of the cocaine experience. Rats given NTI did not show such a preference even though they received cocaine.

To summarize, NTI, a prototypical delta-specific opioid antagonist, blocked cocaine's ability to produce a positive CPP. It can be inferred from that observation that NTI blocked cocaine's ability to establish a positive affective state.

There are some other interesting features of this initial test of a delta-specific antagonist's ability to block psychomotor stimulant's effects. NTI did not by itself establish a place preference unlike other nonspecific opioid antagonists such as naloxone and naltrexone. This unique feature of NTI, compared to the nonspecific antagonists, has important practical implications. A drug that produces a place aversion is apt to be a drug that will not be taken by people. Stated differently, a drug that produces a state that is aversive is not apt to be taken. It is for this reason that naltrexone, although capable of blocking heroin's effects, probably will not be an effective agent for treating heroin addiction because heroin addicts do not comply with the admonition to take naltrexone because naltrexone produces aversive effects. NTI apparently does not suffer this handicap.

EXAMPLE 4

NTI Blocks Cocaine-Induced Facilitation of Responding for Rewarding Brain Stimulation When rats are fixed with chronically indwelling bipolar electrodes for electrical stimulation of the medial forebrain bundle, they will press levers for brief durations of stimulation. The higher the intensity of stimulation, the greater the pressing. Cocaine increases pressing for brain stimulation. These relationships plus extant theory provide the rationale for using pressing for brain stimulation as a means of assessing the reinforcing effects of drugs and assessing which drugs might affect another drug's reinforcing effects.

The particulars of the procedures used herein are briefly summarized. Further information is in Reid (cited above) and Reid et al. (*Life Sciences*, 52, PL67-71 (1993)). Rats were fixed with chronically indwelling bipolar electrodes. Using standard stereotaxic methods, which includes full anesthesia, the tips of the electrode were aimed to stimulate the medial forebrain bundle as it traverses the lateral hypothalamus. With the skull held in a stereotaxic instrument so that a plane between bregma and lamba was perpendicular to the shaft of the electrode, the following stereotaxic coordinates were used: 3.5 mm posterior to brema, 1.6 mm lateral to the midline, and 8.6 mm below the surface of the skull.

The apparatus of these tests was a Skinner box ($24 \times 30 \times 38$ cm) equipped with a lever ($2.5 \times 2$ cm). Each box was fixed with electrical leads and a slip-ring apparatus that allowed the rat to be connected to the electrical stimulator for intracranial stimulation, but allowed the rat to move freely in the box.

Upon full recovery from surgery, rats were trained to press a lever in the Skinner box for electrial stimulation of the brain. The electrical stimulation was 60 Hz sine waves of 0.3 sec. The maximum intensity used was of 50 microAmps. Each lever press delivered one 0.3-sec of brain stimulation.

Just after rats learned to press the lever, the intensity of the brain stimulation was varied. Three intensities were chosen. The lowest intensity was one that was barely sufficient to sustain lever pressing. The highest intensity sustained high rates of pressing, but not the highest rates that a rat can achieve. The medium intensity was about midway between the lowest and the highest. Once a set of intensities were established for each rat, those intensities remained fixed throughout the balance of testing. To illustrate how pressing varied with the intensities, the means of the data for 5 rats are presented. The low intensity chosen was 13.2 microAmps with limits to the range of 10 and 20 microAmps. The low intensity produced 19.5 (with a standard error of the mean of 3.4) presses a minute. The medium intensity was a mean of 18.0 microAmps (range: 15–25) which sustained a mean of 49.2 ($\pm 5.5$) presses a minute. The highest intensity was a mean of 24 microAmps (range: 20–30) sustaining a mean of 75.5 ($\pm 4.1$) presses a minute.

Figure 3:
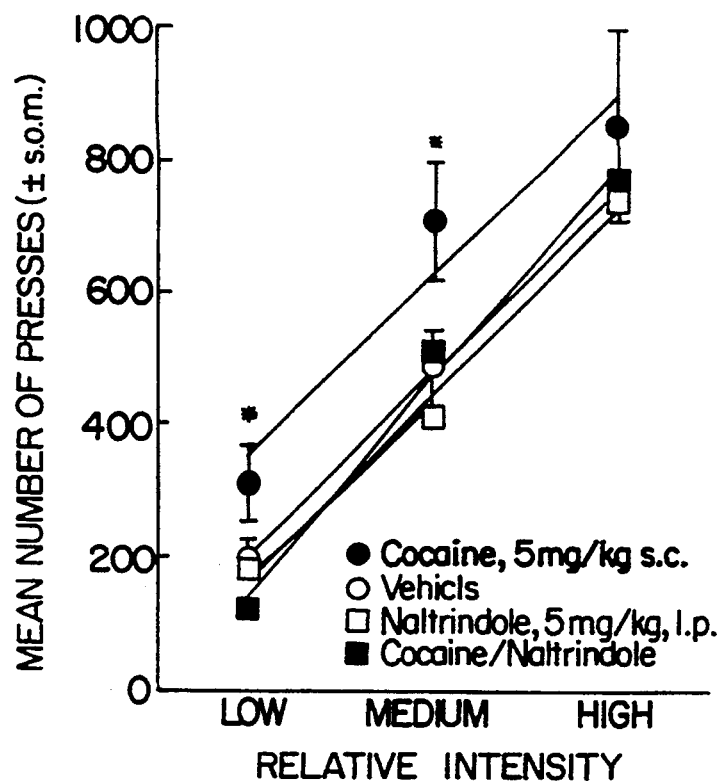
FIG. 3 is a depiction of mean rates of pressing for each of three intensities of brain stimulation under four conditions of dosing.

Each rat was under a daily regimen. They were allowed to press for each of three intensities of brain stimulation for 10 minutes. They were low, medium and high intensities maintaining low, modest and high rates of pressing, respectively (see above and FIG. 3 as rates under vehicle, placebos). They were allowed to press the lever under this daily regimen under level-pressing rates became stable. Then, drugs (or placebos) were administered.

When cocaine was given before one of the daily opportunities to press for brain stimulation, cocaine lead to the expected large increase in pressing. When NTI was given by itself, there was no demonstratable effect. When cocaine and NTI were given, cocaine did not facilitate pressing and levels of pressing appeared similar to that when placebos were given. In brief, NTI blocked cocaine's effects. These results are summarized in FIG. 3.

EXAMPLE 5

Further Tests of NTI's Effects on Cocaine's Ability to Facilitate Pressing for Rewarding Brain Stimulation and Tests of NTI's Effects on Morphine's Ability The data of Example 4 indicated that NTI effectively blocks the reinforcing effects of cocaine. The data, however, are limited by the small numbers of subjects used in the experiment. This experiment is an extension of Example 4 involving more subjects. An additional feature of this testing is a test of the specificity of NTI's effects with respect to cocaine (and eventually addictive phenylisopropylamines) in comparison to morphine's (the prototypical opiate) effects.

The methods of Example 5 were nearly the same as those of Example 4. Rats were fixed, using standard procedures, with chronically indwelling electrodes for stimulation of the medial forebrain bundle. Subsequent to recovery from surgery, they were trained to press for brain stimulation. After each learned to press, they were put on a daily regimen. That daily regimen involved pressing for 5 min at a high intensity of brain stimulation, followed by 5-minute sessions with medium, low, low, medium and then high intensity. Intensities were set for each rat so that pressing rate for the low intensity was rather slow (the low intensity being near lower threshold for maintaining pressing), pressing for the high intensity was at a high rate, and pressing for the medium intensity was between the rate for low and high intensity. Pressing at each intensity was averaged for an index of rat's responsiveness at that intensity.

Injections of cocaine (5.0 mg/kg), which were given daily just before a day's session to some of the rats, produced their characteristic effects, i.e., cocaine increased pressing for stimulation. Injections of morphine (4.0 mg/kg), which were given daily just before a day's session to some of the rats, produced their characteristic effects, i.e., morphine increased pressing for brain stimulation. On a day before the sessions, rats received a dose of naltrindole (10.0 mg/kg, interperitoneally, 20 min before the session).

Figure 4:
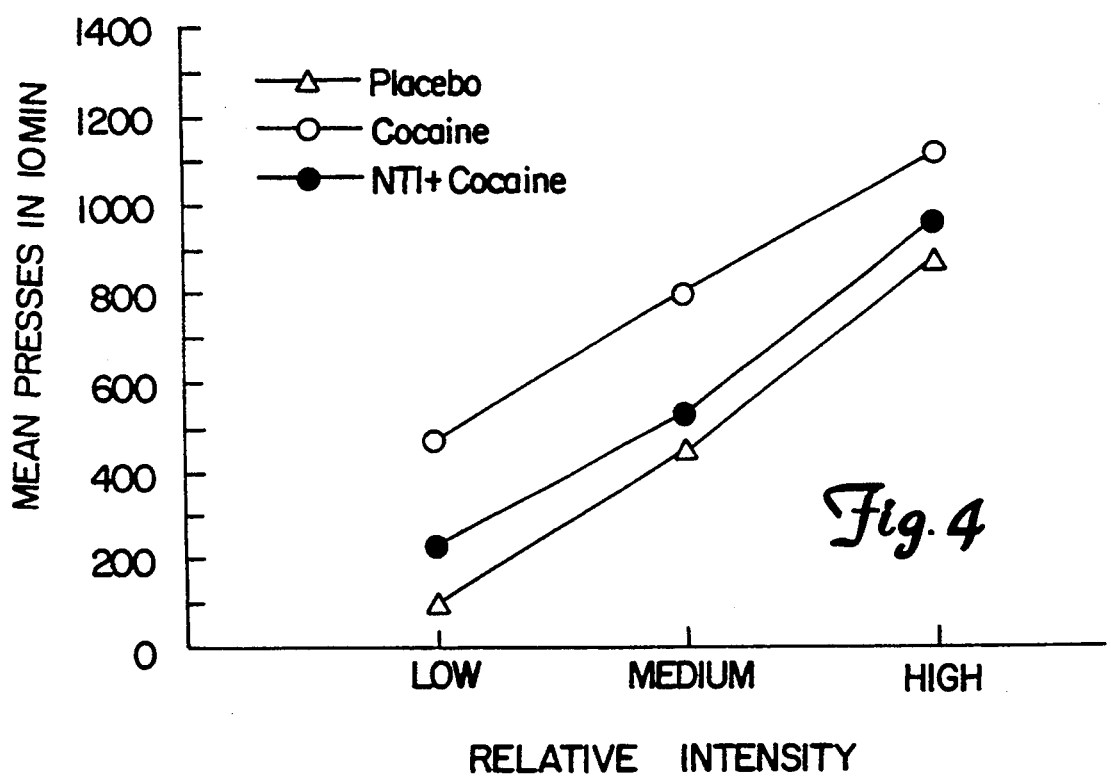
FIG. 4 is a graphical depiction of mean rates of pressing for each of three intensities of brain stimulation by rats under three different conditions of drug administration. Cocaine leads to a marked increase in pressing compared to pressing under the influence of placebo. Notice that naltrindole (NTI) reduced rate of pressing under the influence of cocaine to that similar to rate of pressing under placebo alone.
Figure 5:
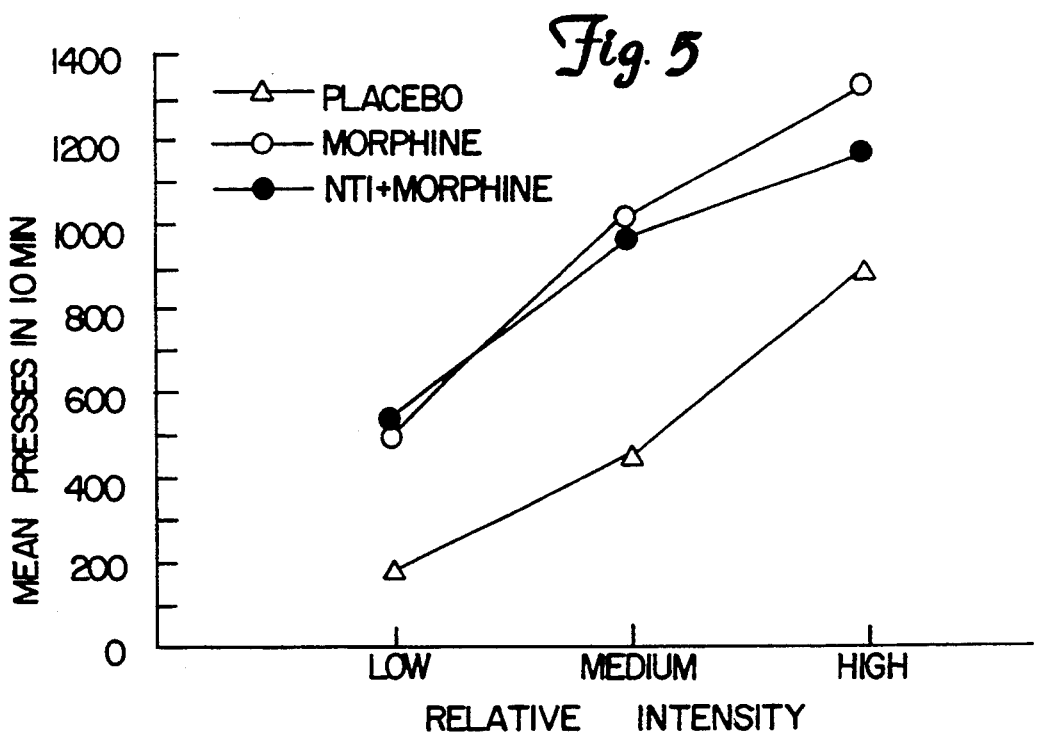
FIG. 5 is a depiction of mean rates of pressing for each of three intensities of brain stimulation. Morphine leads to a marked increase in pressing compared to pressing under the influence of placebo. Naltrindole (NTI) did not markedly or significantly affect rate of pressing when rats were under the influence of morphine.

FIGS. 4 and 5 depict the results. To summarize, NTI blocked the effects of cocaine, but hardly affected the effects of morphine. NTI typically does not affect morphine's analgesic effects. Consequently, it may not be surprising that NTI did not affect morphine's ability to increase pressing for brain stimulation. On the other hand, NTI is an opioid antagonist. From the perspective that NTI is an opioid antagonist and from the perspective that cocaine is widely believed to produce its reinforcing effects by way of dopaminergic activity, the overall results are surprising.

The results of this experiment confirm and extend the results of Examples 3 and 4. The basic finding that NTI blocked cocaine's ability to be reinforcing was verified. The data of this example also show that NTI's effects are quite specific. If NTI's effects were nonspecific, it would be expected that NTI would have interferred with the high rate of pressing characteristic of morphine-facilitated pressing. Since NTI's effects on morphine-facilitated pressing were negligible, it can be concluded that NTI probably does not produce its effects, with respect to cocaine, by way of producing a general malaise, a motor dysfunction, or by interfering with general affective processes of brain. Thus, these data provide further confirmation that delta-specific-opioid processes are salient to cocaine's reinforcement.

EXAMPLE 6

NTI's Effects on Self-Administration of Cocaine

Rats were fixed with chronically indwelling catheters for the delivery of doses of cocaine directly into their veins. Subsequently, the rats were trained to press a lever for small bolus injections of cocaine (0.4 mg/kg of cocaine a lever press with an injection volume of 10 microliters of drug plus saline solution, the drug carrier). Rats were given one-hour opportunities daily to press for cocaine. The rats developed stable rates of pressing for the opportunity to press for cocaine under such a regimen. Also, rats can be given daily opportunities to press for morphine (0.04 mg/kg a lever press).

Of the rats pressing an average of about 11 presses a session, the dose of 3.0 mg/kg of NTI reduced their pressing to less than 3 presses a session. Further, the presses that did occur were generally confined to the first segment of a session, i.e., the rats initiated pressing, but stopped pressing before taking a usual amount of cocaine. Pressing was suppressed the day after injection of NTI as well as the day of injections. Rats, however, returned to their typical rate of pressing with the next daily opportunity to press and without further injections of NTI.

There is a possibility that rats pressing for more cocaine will require larger doses of NTI to interfere with cocaine's ability to sustain its own intake as shown by one rat's performance. Nevertheless, the data all indicate that NTI has a dramatic effect on cocaine's ability to sustain its own intake. As to be expected from the data associated with other tests of NTI and morphine's effects, NTI did not dramatically modify rats' pressing for morphine.

EXAMPLE 7

NTI Blockage of Amphetamine-Induced Facilitation of Responding for Rewarding Brain Stimulation The question addressed in this example is whether or not NTI will modify amphetamine's potential to be reinforcing as NTI modified cocaine's potential.

The test used was very similar to the test of Example 4, with the exception that amphetamine was used rather than cocaine and the test involved two subjects.

Figure 6:
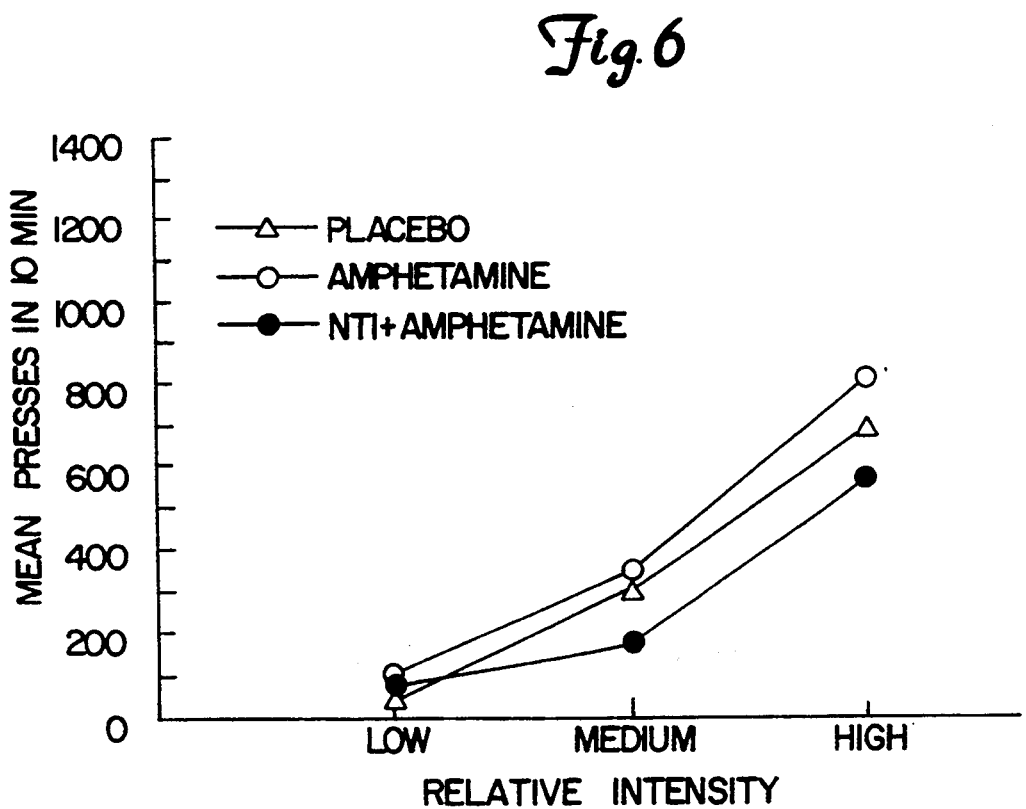
FIG. 6 is a graphic depiction of mean rates of pressing for each of three intensities of brain stimulation. Amphetamine produced increased pressing compared to pressing under the influence of placebo. Naltrindole (NTI) in combination with amphetamine reduced pressing similar to rate under placebo.

The results are depicted in FIG. 6. As expected, amphetamine (2 mg/kg) produced an increment in pressing. As can be seen, the rats pressed somewhat less under the influence of NTI (10 mg/kg) plus amphetamine than they did under the influence of placebos. Although the rats pressed somewhat less under the influence of both drugs, there is little basis for concluding that the rats were debilitated by the combination of drugs.

Although these data are limited in terms of numbers of subjects and size of doses, the results demonstrate that NTI can modulate amphetamine's as well as cocaine's reinforcing effects.

EXAMPLE 8

NTI's Effects on Increasing Pressing for Rewarding Brain Stimulation Caused by MDMA This is a test, using the procedures of Examples 4, 5 and 7 of whether or not NTI will block the effects of MDMA. MDMA is the prototype of another kind of addictive phenylisopropylamine. MDMA produces a conditioned place preference among rats. This conditioned place preference is attenuated but not blocked by naltrexone, a nonspecific opioid antagonist. Given that circumstance, it was not expected that NTI would reduce MDMA's effects with respect to increasing pressing for rewarding brain stimulation, because a nonspecific antagonist is apt to be more powerful (i.e., acts to antagonize more receptors) than a specific one.

The results of this testing, involving six rats, are depicted in Table V.

TABLE V

| Drug | Intensity of Intracranial Stimulation | | |
|---|---|---|---|
| Treatment | Low | Medium | High |
| Placebos | 63 | 254 | 621 |
| MDMA plus Placebo | 288 | 563 | 922 |
| MDMA plus Naltrindole | 98 | 342 | 825 |

Note: The values in the table are mean presses per ten minutes at each intensity of brain stimulation under three different drug conditions.

The data on Table V demonstrate that MDMA increased pressing as would be expected, since MDMA produces a conditioned place preference and is self-administered by both laboratory animals and people. NTI reduced the increased pressing associated with the administration of MDMA. The results are clearest with the low intensity of stimulation. At the lowest intensity of stimulation, all rats under the influence of MDMA showed a dramatic increase in pressing for this near threshold intensity (the average increase is by a factor of four times and the increase is shown with every one of the six rats). Under the influence of both MDMA and naltrindole, pressing at the low intensity is reduced considerably and there is no reliable difference in pressing under the combination of drugs compared to placebo (in fact, half of the rats show a slight reduction in pressing compared to placebo and half show a slight increase). The extent of the reduction with NTI is not as dramatic at the highest intensity, but is nevertheless sufficiently large to conclude that NTI reduces MDMA's effects.

EXAMPLE 9

Effect of BNTX on Cocaine's Reinforcing Potential

The data of Examples 3 through 8 all confirm the conclusion that NTI blocks the addictive properties of psychomotor stimulants. Here, it is demonstrated that a compound of formula II produces similar effects. The methods were those used in Examples 4, 5, 7 and 8, except that 7-benzylidenenaltrexone (BNTX) was used and the number of rats was three.

Figure 7:
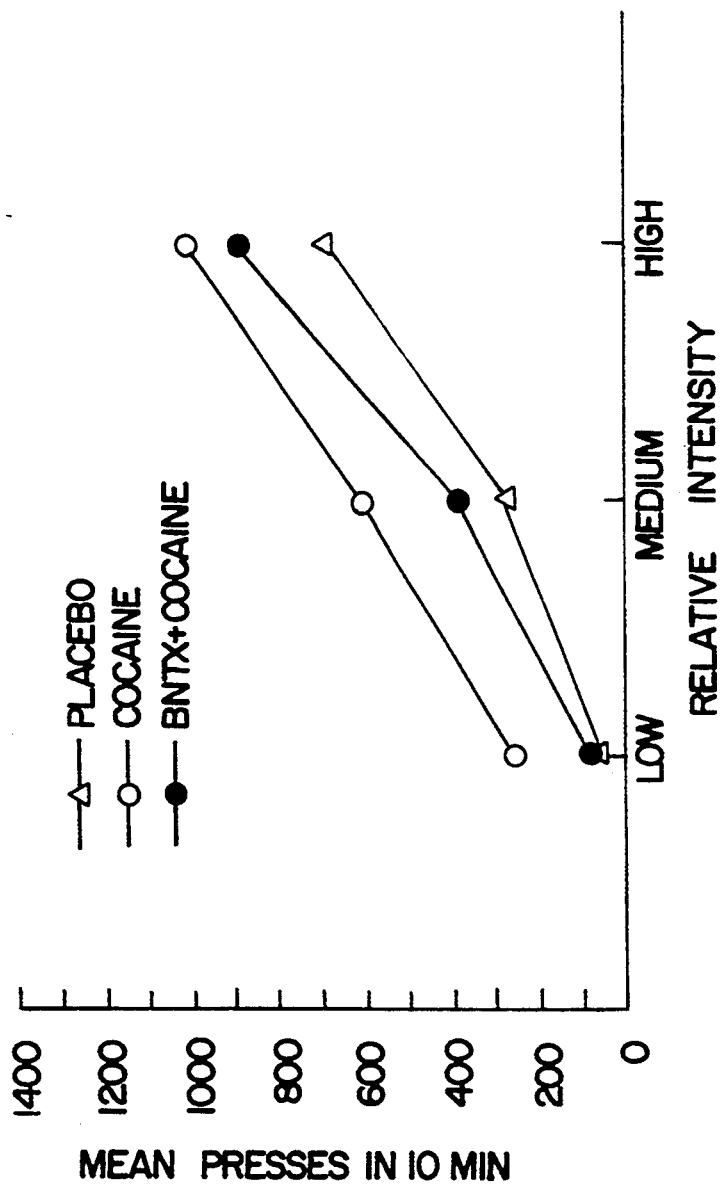
FIG. 7 is a graphic depiction of the effects of BNTX on the ability of cocaine to facilitate responding for rewarding brain stimulation.

The results are depicted in FIG. 7. BNTX (10 mg/kg) reduced cocaine's (5 mg/kg) facilitation of pressing for rewarding brain stimulation in a fashion similar to the reduction observed for NTI. Although these are very preliminary data, the results compel the conclusion that with further testing, it will be shown that BNTX, as well as other specific delta-opioid antagonists of formulas I-III, will effectively mute the reinforcing potential of psycho-motor-stimulant drugs such as cocaine and addictive phenylisopropylamines, i.e., BNTX has similar properties to NTI.

General Conclusions

Despite the facts (a) that the general literature on addictions to cocaine teaches that opioid processes are tangential to cocaine's salient effects, (b) that when broad spectrum (and supposedly powerful) antagonists were tested for their effects on cocaine's effects, they produced either small effects or only attenuated the effects of cocaine without blocking the effects, and (c) that the extant trend toward developing opioids to treat cocaine addiction is toward selecting compounds that have long-lasting agonist effects (i.e., drugs such as buprenorphine which are more like heroin or methadone than an antagonist, with a rationale similar to that associated with methadone maintenance), the experimental data summarized here demonstrates that the delta-specific-opioid antagonists NTI and BNTX are extraordinarily effective in blocking cocaine's salient effects. Further, NTI is effective in muting the salient effects of two addictive phenylisopropylamines. These unexpected discoveries lead, in turn, to the implication that delta-specific-opioid antagonists will be effective for treating addictions to psychomotor stimulants, e.g., cocaine and its congeners and addictive central stimulant phenylisopropylamines.

Also, the present data show that NTI did not, by itself, reduce pressing for brain stimulation. Additionally, as shown in Example 3, NTI did not produce place preferences or place aversions when given as the conditioning agent. In contrast, naloxone and naltrexone, two relatively nonselective opioid antagonists, have been shown to condition place aversions by E. J. Bilsky et al., *Pharmacol. Biochem. Behav.*, 37, 425 (1990) and R. F. Mucha et al., *Brain Res.*, 243, 91 (1982). Also, J. D. Belluzi et al., *Nature*, 266, 556 (1977) and J. M. Stapleton et al., *Physiol. Psychol.*, 7, 427 (1979) have shown that naloxone reduces pressing for rewarding brain stimulation (although the extent of reduction is small). The receptor selectivity, and specificity of NTI evidently makes its effects more neutral with respect to affective responses than these nonselective antagonists. The conclusion that NTI, by itself, does not produce marked effects in these kinds of tests implies, for example, that it would be difficult to ascribe the NTI blockade of cocaine effects to nonspecific effects such as reducing the animal's ability to move, producing a malaise, or blunting all affective processes.

The data indicating that naltrindole is neither reinforcing nor aversive, suggest that naltrindole and other delta-selective opioid receptor antagonists would be likely to exhibit an appropriate profile for use in humans. The data demonstrate the feasibility of development of the present opioid delta antagonists for the treatment of human addictions to psychomotor stimulants such as cocaine and its congeners and addictive phenylisopropylamines.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating cocaine use by a human comprising administering to a human in need of such treatment an amount of a compound of the formula I:

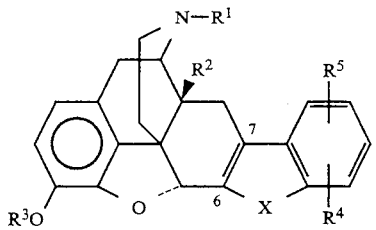 (I)

wherein $R^1$ is $(C_1-C_5)$alkyl, $C_3-C_6$(cycloalkyl)alkyl, $C_5-C_7$(cycloalkenyl)alkyl, aryl, aralkyl, trans$(C_4-C_5)$alkenyl, allyl or furan-2-ylalkyl, $R^2$ is H, OH or $O_2C$-$(C_1-C_5)$alkyl; $R^3$ is H, $(C_1-C_5)$alkyl; or $((C_1-C_5)$alkyl$)CO$; X is O, S or NY, wherein Y is H or $(C_1-C_5)$alkyl; and $R^4$ and $R^5$ are individually H, F, Cl, Br, NCS, $NO_2$, $NH_2$, $(C_1-C_5)$alkyl or $(C_1-C_5)$alkoxy, or together are benzo; and the pharmaceutically acceptable salts thereof; wherein said amount is effective to inhibit the use of cocaine by said human.

2. The method of claim 1 wherein the amount of the compound of formula I is effective to block or reduce the positive reinforcement of cocaine used by said human or the dependence of said human on cocaine.

3. The method of claim 1 wherein $R^1$ is $C_3-C_6$-(cycloalkyl)alkyl and $R^2$=OH.

4. The method of claim 3 wherein $R^3$ is H.

5. The method of claim 4 wherein $R^1$ is cyclopropylmethyl.

6. The method of claim 1 wherein X is NH or O.

7. The method of claim 1 wherein $R^4$ and $R^5$ are H.

8. The method of claim 1 wherein $R^4$ is H and $R^5$ is 5'-NCS.

9. The method of claim 1 wherein the compound of formula I is naltrindole.

10. The method of claim 1 wherein the compound of formula I is naltrindole 5'-isocyanate.

11. The method of claim 1 comprising administering the amount of the compound of formula I in a unit dosage form in combination with a pharmaceutically acceptable carrier.

12. The method of claim 11 wherein the pharmaceutically acceptable carrier is a liquid.

13. The method of claim 11 wherein the unit dosage form comprises a tablet, capsule or solution comprising the compound of formula I.

14. The method of claim 1 wherein the amount of the compound of formula I is administered parenterally.

15. The method of claim 14 wherein the amount of the compound of formula I is administered by injection or by intravenous infusion.

16. The method of claim 14 wherein the amount of the compound of formula I is administered transdermally.

17. The method of claim 1 wherein the amount of the compound of formula I is administered orally.

* * * * *

UNITED STATES PATENT AND TRADEMARK OFFICE
CERTIFICATE OF CORRECTION

PATENT NO. : 5,411,965

DATED : May 2, 1995

INVENTOR(S) : Ried et al.

It is certified that error appears in the above-indentified patent and that said Letters Patent is hereby corrected as shown below:

Column 7 Line 13 Last two columns are incorrectly labeled, it should read --$R^4$  $R^5$-- therefor.

Signed and Sealed this

Thirteenth Day of August, 1996

Attest:

BRUCE LEHMAN

Attesting Officer    Commissioner of Patents and Trademarks